(12) United States Patent
Nohilly et al.

(10) Patent No.: US 6,951,569 B2
(45) Date of Patent: *Oct. 4, 2005

(54) SURGICAL BALLOON HAVING VARYING WALL THICKNESS

(75) Inventors: Martin Nohilly, Murray Hill, NJ (US); Dorothy Dion, West Orange, NJ (US)

(73) Assignee: Ethicon, Inc., Somerville, NJ (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/326,044

(22) Filed: Dec. 20, 2002

(65) Prior Publication Data

US 2003/0153940 A1 Aug. 14, 2003

Related U.S. Application Data

(63) Continuation-in-part of application No. 09/749,077, filed on Dec. 27, 2000, now Pat. No. 6,607,545.

(51) Int. Cl.[7] .............................................. A61M 29/00
(52) U.S. Cl. ....................... 606/193; 606/191; 606/192; 606/27; 606/28; 606/41
(58) Field of Search ................................ 606/193, 191, 606/192, 194, 195, 198, 27, 28, 41, 33; 600/549; 128/836; 604/96.1; 607/105, 113, 138, 98, 99, 96

(56) References Cited

U.S. PATENT DOCUMENTS 3,779,241 A * 12/1973 Vennard et al. ............. 128/836
3,923,051 A * 12/1975 Soichet ....................... 128/836
3,924,628 A    12/1975 Droegemueller et al.
5,449,380 A    9/1995  Chin
5,501,681 A    3/1996  Neuwirth et al.
5,643,311 A *  7/1997  Smith et al. ................. 606/193
5,868,735 A    2/1999  Lafontaine
5,891,457 A    4/1999  Neuwirth
5,902,251 A    5/1999  vanHooydonk
5,947,991 A *  9/1999  Cowan ....................... 606/191
5,954,714 A    9/1999  Saadat et al.
5,964,755 A    10/1999 Edwards
6,026,331 A    2/2000  Feldberg et al.
6,216,704 B1   4/2001  Ingle et al.
6,302,904 B1 * 10/2001 Wallsten et al. ............ 607/105

FOREIGN PATENT DOCUMENTS

WO    WO 00/54829    9/2000

* cited by examiner

*Primary Examiner*—Vy Bui

(57) ABSTRACT

A surgical balloon is provided for insertion into a uterus that includes a substantially continuous outer wall defining an exterior surface of the balloon on a first side and an interior hollow of the balloon on a second side, with the outer wall being formed from a stretchable elastic material and being stretchable by pressure within the inner hollow between a collapsed state and an expanded state. The substantially continuous outer wall has a base portion for coupling with shaft, an intermediate portion adjacent the base portion and an end portion at a distal end of the balloon and adjacent the intermediate portion. The base portion has a first primary wall thickness, the intermediate portion has a second primary wall thickness, and the end portion has a third primary wall thickness.

10 Claims, 5 Drawing Sheets

SURGICAL BALLOON HAVING VARYING WALL THICKNESS

CROSS REFERENCE TO RELATED APPLICATIONS

The present invention is a continuation-in-part of earlier filed U.S. patent application Ser. No. 09/749,077, now U.S. Pat. No. 6,607,545, filed on Dec. 27, 2000 and entitled "Conformal Surgical Balloon With Varying Wall Expansibility", which is incorporated herein by reference.

FIELD OF THE INVENTION

The present invention relates to surgical balloons, and more particularly to balloons suitable for introduction into a body cavity for containing a thermally conductive media used for ablation of cells within the cavity.

BACKGROUND OF THE INVENTION

Surgical balloons have a variety of uses, including the containment of fluids used to necrose cells lining a body cavity. For example, it has now become common to treat excessive menstrual bleeding (menorrhagia) by inserting a balloon catheter into the uterus, filling the balloon with a thermally conductive media and heating or cooling the media to thermally kill the endometrial lining of the uterus. An exemplary thermal ablation process and apparatus utilizing a surgical balloon are described in U.S. Pat. No. 5,501,681 to Neuwirth et al.

As shown in U.S. Pat. No. 5,501,681, known surgical balloons are typically formed from latex, have a bulb shape, and inflate in a manner which enlarges the bulb shape uniformly to an approximately spherical or bulbous shape. In contrast, the uterine cavity is Y-shaped in cross-section. The material composition of known balloons is somewhat inelastic, preventing the balloons from readily conforming to the intra-uterine space. As a result, known bulbous surgical balloons do not inflate to contact the entire endometrial lining, in particular, in the area of the uterine cornua. This lack of contact may result in a portion of the endometrial lining escaping treatment.

It is therefore an object of the present invention to provide an improved surgical balloon that exhibits an increased contact area with a body cavity into which it is inserted when the balloon is inflated.

SUMMARY OF THE INVENTION

A surgical balloon is provided for insertion into a uterus. The surgical balloon includes a substantially continuous outer wall defining an exterior surface of the balloon on a first side and an interior hollow of the balloon on a second side, with the outer wall being formed from a stretchable elastic material and being stretchable by pressure within the inner hollow between a collapsed state and an expanded state. The substantially continuous outer wall has a base portion for coupling with shaft, an intermediate portion adjacent the base portion and an end portion at a distal end of the balloon and adjacent the intermediate portion. The base portion has a first primary wall thickness, the intermediate portion has a second primary wall thickness, and the end portion has a third primary wall thickness.

According to one embodiment, the wall thickness of the end portion is about 3 to 5 mil, according to another embodiment, wall thickness of the intermediate portion is about 4–6 mil, and in yet another embodiment, the wall thickness of the base portion is about 5–10 mil.

According to yet another embodiment, the second primary wall thickness is less than the first primary wall thickness, and the third primary wall thickness is less than the first and second primary wall thicknesses.

In an alternate embodiment, the end portion is substantially hemispherical in shape.

Also provided is a surgical balloon for insertion into a uterus including a substantially continuous outer wall defining an exterior surface of the balloon on a first side and an interior hollow of the balloon on a second side, with the outer wall being formed from a stretchable elastic material and being stretchable by pressure within the inner hollow between a collapsed state and an expanded state. The substantially continuous outer wall has a base portion for coupling with a catheter, and a substantially hemispherical shaped end portion positioned at a distal end of the balloon and adjacent the first portion. The end portion has a primary wall thickness less than a primary wall thickness of the base portion.

A surgical balloon is also provided for insertion into a uterus having a substantially continuous outer wall defining an exterior surface of the balloon on a first side and an interior hollow of the balloon on a second side, with the outer wall being formed from a stretchable elastic material and being stretchable by pressure within the inner hollow between a collapsed state and an expanded state. The substantially continuous outer wall has a base portion for coupling with a catheter, and an end portion at a distal end of the balloon. The end portion has a primary wall thickness less than a primary wall thickness of the base portion.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
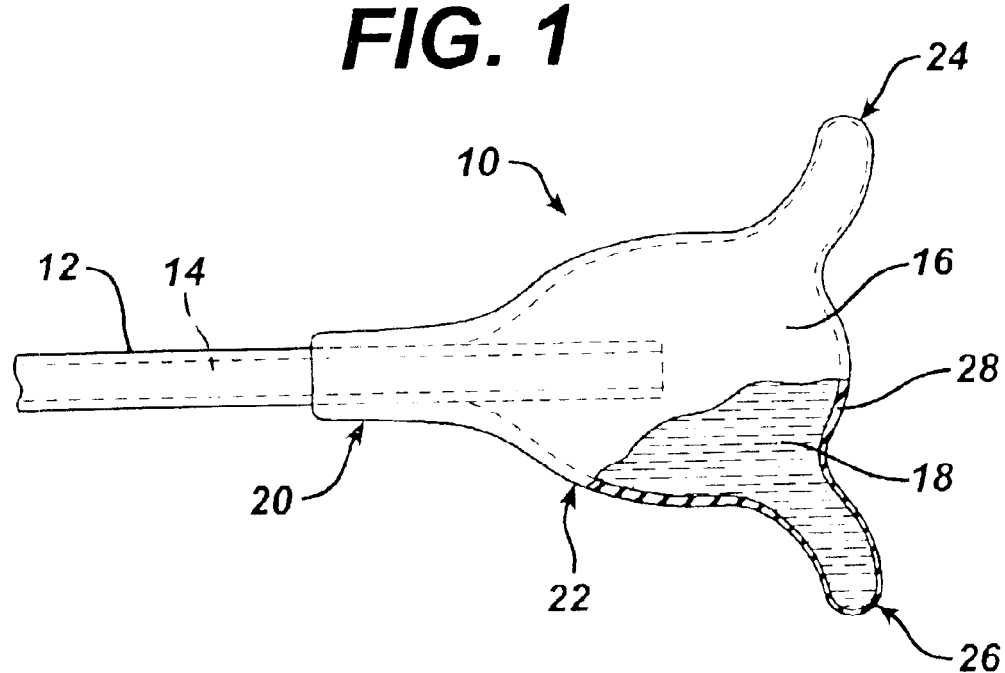
FIG. 1 is a plan view of an inflated surgical balloon in accordance with a first exemplary embodiment of the present invention.

FIG. 1 shows a surgical balloon 10 disposed on the end of a catheter 12. The catheter 12 has a lumen 14 that communicates with the interior hollow 16 of the balloon 12 and permits the infusion of a thermally conductive fluid 18 into the balloon 10 under pressure. As is known in the art, surgical balloons may be used to perform surgical procedures, such as endometrial ablation to cure menorrhagia. U.S. Pat. No. 5,954,714 is incorporated herein by reference for its teachings on the use of surgical balloons for endometrial ablation.

The balloon 10, as described herein, can be used in place of conventional bulb-shaped balloons to perform ablation procedures. More particularly, after the balloon 10 is introduced into the uterus, a pressurized thermally conductive fluid 18, e.g., saline solution, may be used to inflate the balloon 10 within the uterus, followed by heating or cooling of the fluid to thermally cauterize cells in contact with the balloon 10. The balloon 10 is preferably preformed to have a specific shape, such that when the balloon is inflated, it conforms to the walls of the intra-uterine space. The balloon 10 has a base 20 that is adhered to the catheter 12 by an adhesive or by plastic welding. The body 22 of the balloon 10 extends from the base 20 and has left and right extensions 24, 26. As can be appreciated from FIG. 1, the outer three-dimensional shape of the balloon 10 mimics the interior hollow of a uterus when the balloon 10 is inflated. In this manner, the balloon 10 of the present invention can more completely fill the hollow of the uterus into which it is inserted and contact a greater surface area relative to a bulb shaped balloon of the prior art. More particularly, the body 22 may extend from the isthmus to the fundus with the left and right extensions 24, 26 inserting into the uterine cornua. The greater contact area that may be achieved with the balloon 10 of the present invention provides for greater thermal transfer and more complete endometrial ablation.

FIG. 1 shows a portion of the wall 28 of the balloon 10 which has a varying thickness. More specifically, the balloon wall 28 is thick proximate the base 20 where it provides firm attachment to the catheter 12 and where it has no need to expand. The wall 28 is thinnest in those areas requiring maximum expansion, such as the extensions 24, 26, and of intermediate thickness in those areas requiring intermediate expansion, e.g., body 22. That is, in response to a given pressure, a thinner wall will expand outwardly more than a thicker wall. By varying the wall thickness, the balloon 10, which is bulb-shaped when deflated, can assume another shape, e.g., mimicking the intra-uterine space, when inflated. This shape transition of the balloon 10 occurs under the influence of the inherent expansion characteristics of the balloon 10, rather than in response to resistance to expansion exerted by the body cavity. Because the balloon 10 readily assumes a complementary shape to the body cavity in which it is placed, the balloon 10 conforms to the cavity shape without exerting as much pressure on the body cavity as conventional balloons. In addition, an even pressure is exerted by the balloon 10 across the internal surface of the uterus promoting consistent and even contact therebetween which translates to a uniform ablation depth of the cells.

As an alternative to or in addition to variations in wall thickness giving rise to local variations in expansibility, the wall 28 may be treated with heat, radiation or chemicals to achieve the same effect. More particularly, the balloon 10 can be made from polyurethane with a selected area exposed to heat in a temperature range of 260° F. to 280° F. by inserting the balloon 10 into an apertured mask made from aluminum or steel and exposing the balloon 10 to a heat source which will effect only the unmasked area. Alternatively, the balloon 10 may be installed upon a stretching frame and selected surfaces subsequently branded with heated dies. Alternatively, the balloon 10 may be stretched upon a frame and subjected to chemicals such as, dimethyl sulfoxide or tetrahydrofuran, that are printed on, brushed, dabbed or sprayed on through a mask.

The balloon 10 may be blow molded from polyester or polyethylene resins; dip molded from silicones, natural latex rubber or polyisoprene, a synthetic rubber; extrusion molded from silicone; injection molded from polyurethanes or silicones; or formed by heat sealing sections (patterns) together. Currently, the preferred method of manufacture is dip molding using natural latex rubber or polyisprene. Other compounds from which the balloon 10 can be made using one or more of the foregoing processes are polyether block amides, polyolefins and co-polyesters.

As referred to above, the balloon 10 can be formed by heat sealing, viz., by cutting patterns of a sealable expandable material into specific shapes and then heat sealing the edges of the two identical shapes together. This can produce a structure, which has a volume between the top and bottom patterns. An alternate method is to place two sheets of material together, one on top of the other. A formed die is then placed on either side of the two sheets, and the die is heated to melt the sections of the sheets between the corresponding sections of the die. This area creates a seal when it cools. The shape or configuration of the die determines the shape of the balloon 10.

The balloon 10 of the present invention can be used in hot ablation procedures and in cryoablation. Materials, which are best suited for hot ablation procedures, would include polyisoprene, silicone and natural latex rubber. The material best suited for use in cold ablation procedures would be silicone.

Polyurethane, in contrast to the latex compounds that have previously been used to make surgical balloons, is highly elastic and permits the balloon 10 to conform readily to the intrauterine space, even with minimal or no variations in flexibility of the wall 28. Accordingly, the present invention is intended to include the use of polyurethane to produce a surgical balloon with either constant or varying wall thickness to insure low pressure conformation to the intrauterine shape.

Figure 2:
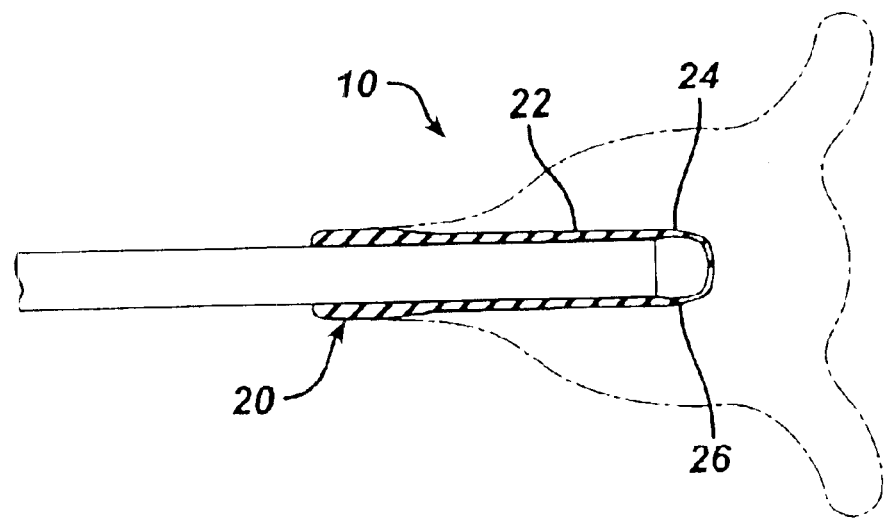
FIG. 2 is a cross-sectional view of the balloon of FIG. 1 in a deflated condition and showing the inflated condition in phantom.
Figure 3:
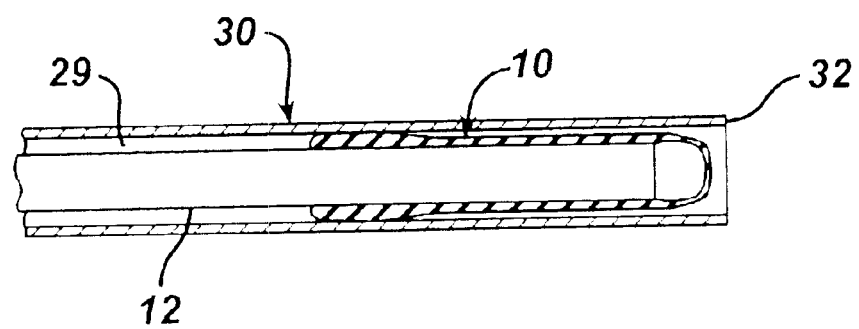
FIG. 3 is a cross-sectional view of the balloon of FIG. 2 stored within a cannula.

FIG. 2 illustrates the balloon 10 of FIG. 1 in a deflated state and the left and right extensions 24, 26 appearing as internal surface indentations due to wall thinning in that area. The thickness of the wall 28 ramps down from the base 20 (which is thickest) to the body 22 (which is of intermediate thickness) and then to the extensions 24, 26 (which have the thinnest walls). It should be appreciated that the variation in the thickness of the wall 28 depicted in FIGS. 1, 2 and 3 is exaggerated for the purposes of illustration. In general, it is preferable for the thinning of the wall 28 to occur inside the balloon 10, in a symmetrical fashion. This will produce an even expansion of the outer surface. The transition from thin wall section to thick wall section will be smooth on the external surface of the balloon 10 in this configuration. Sharp changes in wall thickness will produce areas of high stress concentration, which will weaken the balloon 10 at those sites. This could lead to balloon failure during expansion.

As can be appreciated from FIG. 3, the deflated balloon 10 is readily accommodated within the lumen 29 of a cannula or introducer tube 30 that is used to facilitate introduction and deployment of the catheter 12 and balloon 10 into the uterus of a patient. More particularly, the cannula 30 can be slipped through the uterine os, followed by urging of the catheter 12 forward to deploy the balloon 10 beyond open tip 32 of the cannula 30. In the alternative, the cannula 30 can be withdrawn backward off of the balloon 10, exposing it in place. Once the balloon 10 is unconstrained by the cannula 30, it can be expanded under the influence of the infusion of thermally conductive fluid into the balloon 10, inflating it to the shape shown in FIG. 1.

A commonly owned copending application Ser. No. 09/749,180, entitled CONFORMAL SURGICAL BALLOON and filed contemporaneously herewith by the present inventors, discloses a surgical balloon that conforms to the intra-uterine space aided by its preformed shape, such copending application being incorporated herein by reference. The present invention therefore contemplates a preformed surgical balloon (mimicking the uterine cavity shape) wherein the wall thickness and/or wall elasticity varies in accordance with the teachings of the present application, to aid in permitting the balloon to conform to the body cavity in which it is inflated. In particular, it is beneficial for the extensions 24, 26 of such a preformed balloon to have a thinner wall thickness and/or greater expansibility than the remainder of the balloon. Besides aiding the expansion of the extensions 24, 26 into the uterine cornua, the thinned extensions 24, 26 of a deflated preformed balloon can be more readily and compactly folded for storage within the cannula 30 and can be deployed more readily.

In the description to follow, a numbering convention will be used wherein elements having a similar function to a preceding embodiment shall have the same reference numerals increased by one hundred.

Figure 4:
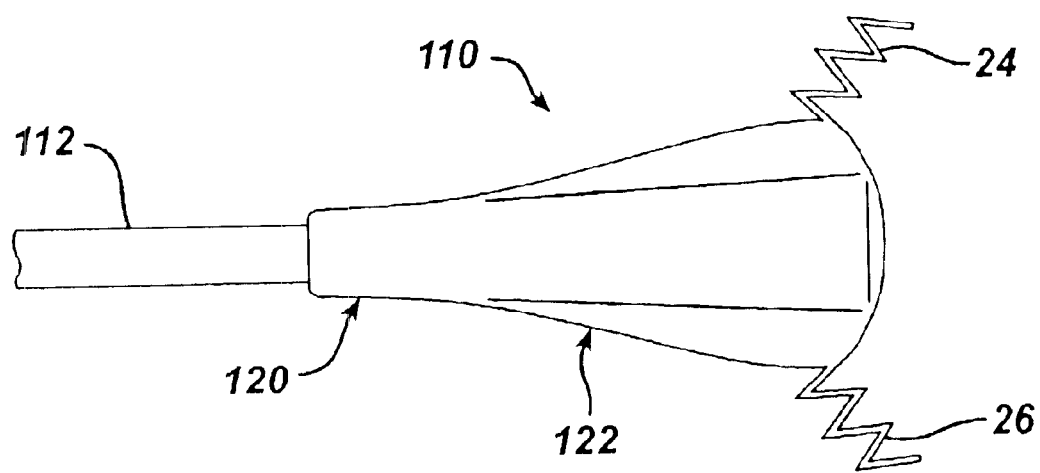
FIG. 4 is a plan view of an alternative embodiment of a balloon in accordance with the present invention.

FIG. 4 shows how a preformed balloon 110 with thinned extensions 124, 126 is folded to allow storage in the cannula 30 (see FIG. 3) and to facilitate a controlled unfolding and deployment when the balloon 110 is pushed out of the cannula 30 into the uterus. More specifically, the extensions 124, 126 are folded in a zig-zag configuration. Preferably, the balloon 110 is stored in a folded configuration that provides for a sequenced unfolding that properly positions the balloon 110 within the uterus to facilitate optimal balloon-to-endometrial lining contact when the thermally conductive media is infused into the balloon 110, inflating it and filling the intra-uterine space. When applied in the treatment of a body cavity having a directional sense, such as the uterus, the balloon 110 has a shape that requires orientation relative to the specific orientation of the body cavity in which it is deployed. The cannula 30 (see FIG. 3) and/or the catheter 112 are therefore preferably provided with an orientation marking that allows the surgeon to insert the balloon 10 in the proper orientation relative to the patient. To maintain the relative position of the catheter 112 and the cannula 30, it is preferred that each be keyed relative to the other, e.g., that the catheter 112 be provided with a longitudinal ridge that fits within a mating guide way in the cannula 30. In this manner, the orientation of the balloon 110 is preserved, while the balloon 110 is rotationally fixed relative to the cannula 30 and, in the case of a folded preformed balloon, avoiding inadvertently disturbing the folded position of the balloon 110.

The selection of material for the balloon 10, 110 insures that the balloon 10, 110 will not stick to itself or the cannula 30 after prolonged storage within the cannula 30. Alternatively, the balloon 10, 110 may be coated with a conventional biocompatible, non-allergenic lubricant, such as talc, cornstarch or low viscosity silicone, preferably air cured to prevent self-adhesion. In order to promote deployment of a folded balloon 110, it is preferably folded in a manner that minimizes overlap, severity of fold angle and compression forces that exceed the elastic limit of the material at fold lines. In addition, it is preferable that the extensions 124, 126 be folded at intervals that are smaller in length than the spacing between any opposed surfaces within the uterine cavity that could trap the extensions 124, 126 in an unfolded condition, e.g., between the walls of the uterine cornua or between the body of the balloon 110 and the uterine wall.

Figure 5:
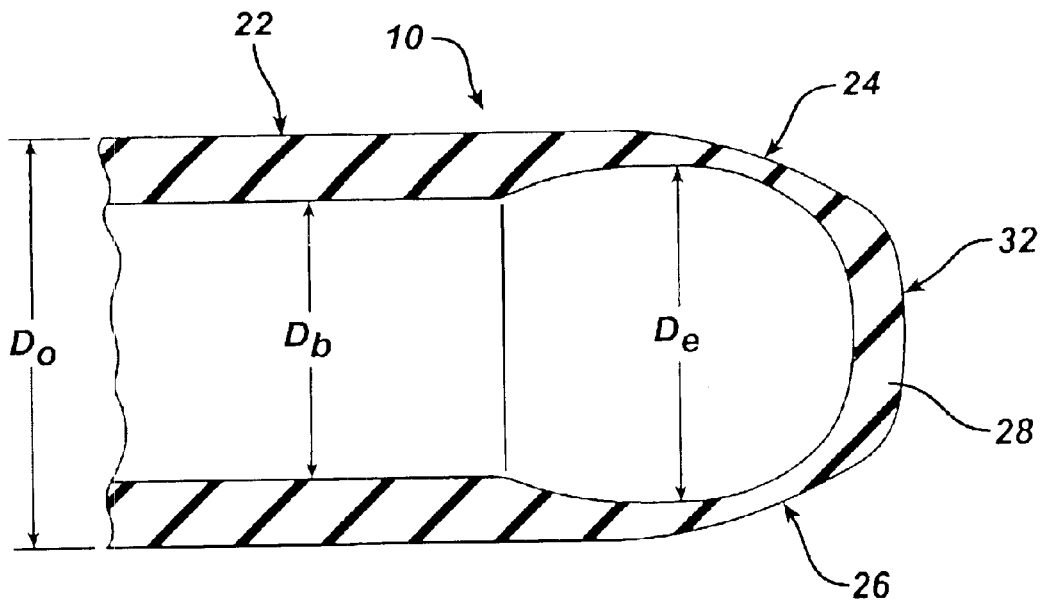
FIG. 5 is an enlarged, cross-sectional view of the tip of the deflated balloon of FIG. 1.

FIG. 5 shows a distal fragment of the balloon 10 of FIG. 3 illustrating how the wall 28 thickness may be selectively varied in accordance with the present invention. More specifically, the thickness of the wall 28 at the tip 32 and body 22 portions is thinned in the area of the extensions 24, 26 by varying the internal diameter of the balloon 10 from $D_b$ to $D_e$ with the outer diameter $D_o$ remaining constant.

Figure 6:
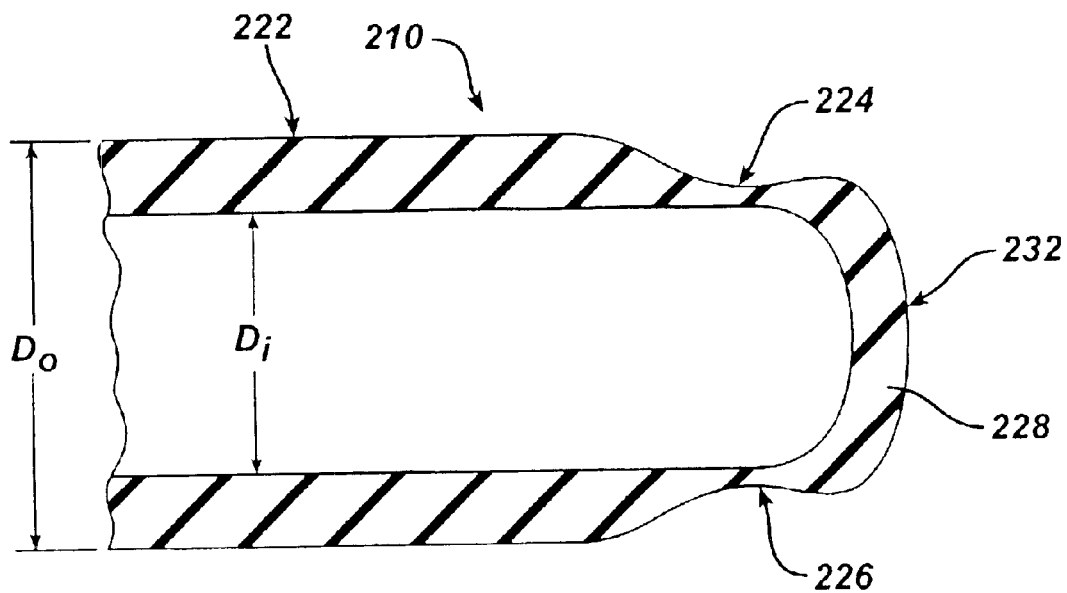
FIG. 6 is an enlarged, cross-sectional view of the tip of an alternative embodiment of the balloon of FIGS. 1 and 5 in accordance with the present invention.

FIG. 6 illustrates an alternative approach to that shown in FIG. 5, wherein the outer diameter $D_o$ of a balloon 210, decreases from that present on body 222 portion to a lesser diameter associated with extensions 224, 226, with the internal diameter $D_i$ remaining constant.

Figure 7:
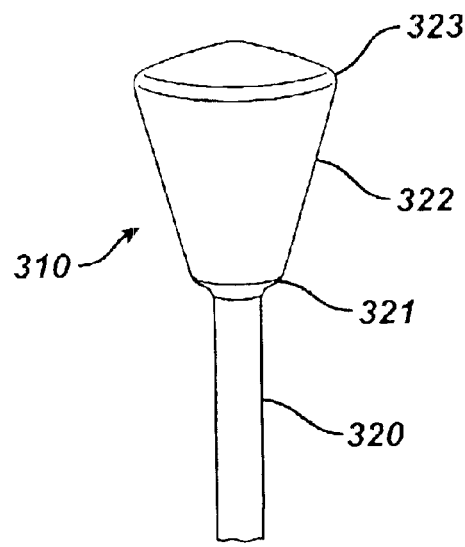
FIG. 7 is a plan view of a surgical balloon in accordance with an alternative exemplary embodiment of the present invention.
Figure 8:
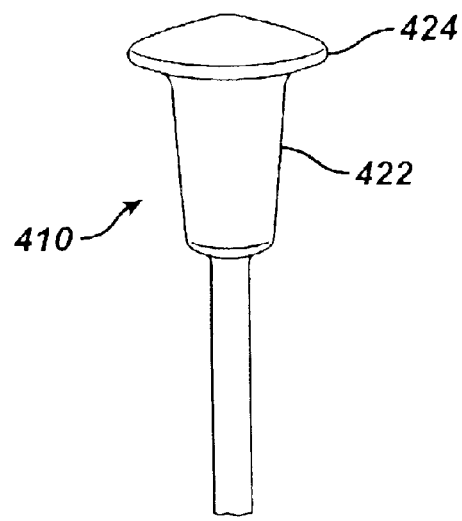
FIG. 8 is a plan view of a surgical balloon in accordance with another alternative embodiment of the present invention.
Figure 9:
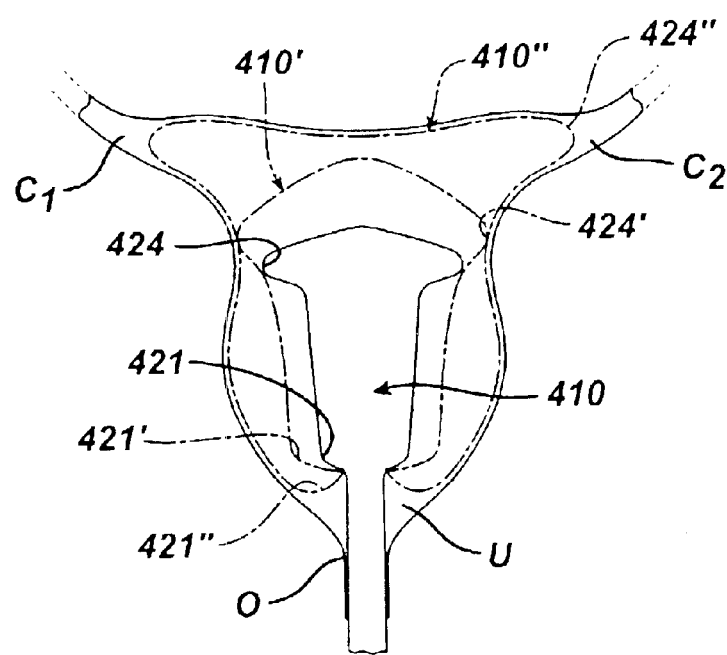
FIG. 9 is a diagrammatic view of the balloon of FIG. 8 at three stages of inflation within a uterine cavity.

FIG. 7 shows a balloon 310 in accordance with the present invention and having an outwardly flaring body 322, the upper peripheral edge 323 of which is intended to extend into the uterine cornua of a patient. The body 322 is axially symmetric, i.e., generally bell-shaped. The shape of the balloon 310 can be determined by varying wall expansibility and/or pre-forming, such that the balloon 310 shown in FIG. 7 could be in the partially inflated state, i.e., having assumed that shape due to selected localized expansion characteristics of the wall of the balloon 310. Alternatively, the balloon 310 may be pre-formed, such that the shape shown is present when the balloon is inflated. In the case of a pre-formed balloon 310 having an uninflated shape as shown, variations in wall expansibility may be incorporated therein in order to further assist the balloon 310 in conforming to the body cavity when it is more fully inflated. When inflated, the overall shape of the balloon 310 and corresponding distribution of flexible wall material allows the upper peripheral edge 323 to expand out into the cornua. The body 322 flares out rapidly from the base 320 to a lower circumference 321 to increase contact with the uterus proximate the uterine os. This effect is illustrated in FIG. 9 described below:

FIG. 8 shows a balloon 410 having a shape similar to the balloon 310 of FIG. 6, but with an expandable upper flange 424 to facilitate expansion into the uterine cornua. FIG. 9 illustrates the balloon 410 within a uterine cavity U, in the uninflated state, in an intermediate state of inflation 410' (dotted) and inflated almost completely 410'=(dotted). As the balloon 410 is inflated, the expansible flange 424, (424', 424'=) approaches and enters the uterine cornua $C_1$, $C_2$. Simultaneously, lower circumference 421, (421', 421'=) immediately expands outwardly to contact the uterine cavity U proximate the os O. Depending upon the shape of the uterine cavity U, the lower circumference 421'=may project downwardly to fill the space between the base 420 and the uterine cavity U proximate the os O. Alternatively, the expansion of the balloon 410 will push the base 420 in an outward direction (to a lesser degree of insertion) such that the balloon 410 will establish maximum contact with the uterine cavity U. Accordingly, surgical balloons 10, 110, 210, 310, 410 establish greater contact with the uterine cavity U more quickly and completely than a conventional bulb-shaped balloon. Since the balloons 10, 110, 210, 310, 410 more readily inflate to a shape approximating the cavity into which they are inserted, greater contact area at a more even, higher pressure is achieved, assuring better thermal transfer.

It should be appreciated that the present invention contemplates a balloon 10, 110, 210, 310, 410 with a symmetrical radial thinning or treatment such that the thinned area, if inflated outside the body, would assume a toroidal, radially symmetric shape. If the same balloon were inflated within the body, e.g., the uterus, then the thinned area would be constrained by the cavity shape such that the extensions 24, 26 (224, 226) can extend into the uterine cornua. Under such circumstances, the balloon will be radially symmetric such that there is no need to provide a means to radially align the balloon to the uterus.

Alternatively, the thinning or treatment of the balloon 10, 110, 210 may be localized such that the extensions 24, 26 (124, 126 and 224, 226) project out like fingers. In that case, the alignment means referred to above in reference to FIG. 4 is preferred in order to align the balloon 10, 110, 210 to the body cavity.

Figure 10:
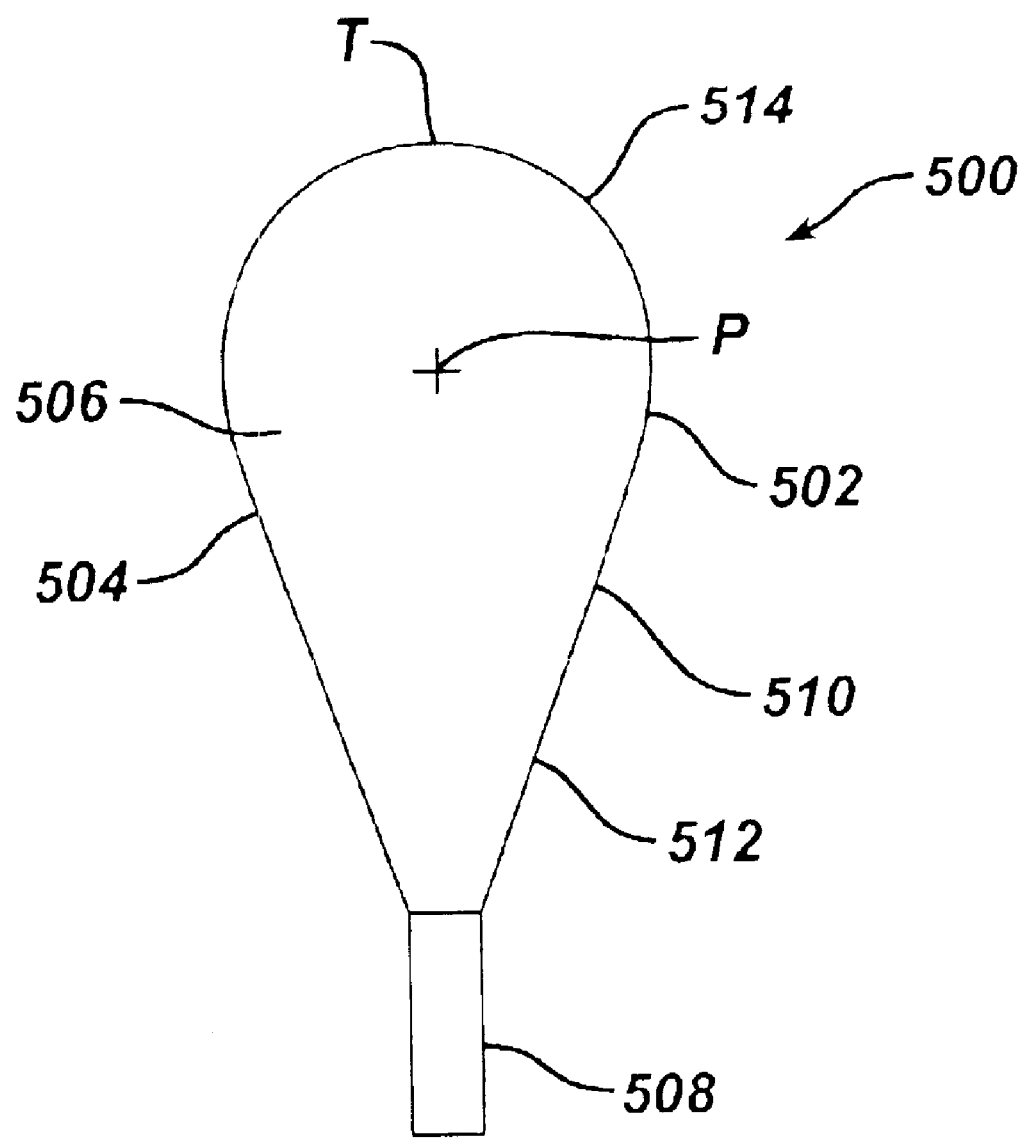
FIG. 10 is a plan view of an alternative embodiment of a balloon in accordance with the present invention.

Referring now to FIG. 10, yet another embodiment of a novel surgical balloon 500 is provided the outer walls of which vary in thickness at specified locations. The balloon has a substantially continuous outer wall 502 defining an exterior surface 504 of the balloon on a first side, and defining an inner hollow 506 of the balloon on a second side. The balloon 500 further includes a base portion 508, and a body portion 510 including an intermediate portion 512 and an end portion 514. In the illustrated embodiment, the end portion 514 substantially forms a hemispherical shape relative to center point P. The end portion may also simply be substantially symmetrical about a distal tip T of the balloon, which could constitute more or less than a hemisphere. As will be described in further detail below, the continuous outer wall of the balloon 500 decreases in thickness from the base portion to the end portion, with each successive portion having a primary wall thickness less than that of the one before. For the purposes of this disclosure, "primary wall thickness" of a designated portion refers to the wall thickness of that portion, excluding any standard tolerance variations and any transition area to an adjacent portion having a different primary wall thickness In a preferred embodiment, the balloon is a dipped silicon balloon that may be manufactured by well known single or multiple dip processes in which the dipping parameters and orientations are controlled to yield the desired thickness. Injection molding or other molding techniques may also be used. The primary wall thickness of the base portion is from 5–10 mil, the primary wall thickness of the intermediate portion is from 4–6 mil, and the primary wall thickness of the end portion is from 3–5 mil. Although the ranges above appear to overlap, it is to be understood that primary wall thickness of end portion will be less than the primary wall thickness of the intermediate portion, which in turn will be less than the primary wall thickness of the base portion; for example 8 mil, 5 mil and 4 mil respectively. It is also to be understood that the thickness of a distal tip portion T of the balloon may have a wall thickness greater than that of the end portion as a result of the inherent effects of well known balloon dipping processes. Such a tip portion will not adversely affect balloon performance as described below, and is excluded when considering the "primary wall thickness" of the end portion.

It has been found that a balloon of the type described above is advantageous in that the end portion, particularly when hemispherical in shape, will expand more than the intermediate portion to conform better to the inner contour of the upper portion of the uterus, to thereby better fill both uterine cornua. In this manner, contact area is increased making the treatment more effective.

It should be understood that the embodiments described herein are merely exemplary and that a person skilled in the art may make many variations and modifications without departing from the spirit and scope of the invention as defined in the appended claims. All such variations and modifications are intended to be included within the scope of the present invention as defined in the appended claims.

What is claimed is:

1. A surgical balloon for insertion into a uterus, comprising:

a substantially continuous outer wall defining an exterior surface of the balloon on a first side and an interior hollow of the balloon on a second side, the outer wall being formed from a stretchable elastic material and being stretchable by pressure within the inner interior hollow between a collapsed state and an expanded state;

the substantially continuous outer wall having a base portion for coupling with a shaft, an intermediate portion adjacent the base portion and an end portion at a distal end of the balloon and adjacent the intermediate portion, left and right extensions configured for insertion into the uterine cornua when the surgical balloon is in the expanded state, the extensions being spaced from each other and lying on either side of the end portion, and intermediate portions lying in between the base portion and the left and right extensions;

wherein the base portion has a first primary wall thickness, the intermediate portions has have a second primary wall thickness, and the end portion has a third primary wall thickness, the left and right extensions have a fourth primary wall thickness, and the fourth primary wall thickness is less than the third primary wall thickness.

2. The surgical balloon according to claim 1, wherein the wall thickness of the end portion is about 3 to 5 mil.

3. The surgical balloon according to claim 2, wherein the wall thickness of the intermediate portion is about 4–6 mil.

4. The surgical balloon according to claim 3, wherein the wall thickness of the base portion is about 5–10 mil.

5. The surgical balloon according to claim 1, wherein the second primary wall thickness is less than the first primary wall thickness, and the third primary wall thickness is less than the first and second primary wall thicknesses.

6. The surgical balloon according to claim 1, wherein the end portion is substantially hemispherical in shape.

7. A surgical balloon for insertion into a uterus; comprising:

a substantially continuous outer wall defining an exterior surface of the balloon on a first side and an interior hollow of the balloon on a second side, the outer wall being formed from a stretchable elastic material and being stretchable by pressure within the inner interior hollow between a collapsed state and an expanded state;

the substantially continuous outer wall having a base portion for coupling with a catheter, and a substantially hemispherical shaped end portion positioned at a distal end of the balloon and adjacent the base portion, and left and right extensions configured for insertion into the uterine cornua when the surgical balloon is in the expanded state, the extensions being spaced from each other and lying on either side of the end portion, wherein the left and right extensions have a primary wall thickness less than a primary wall thickness of the end portion.

8. A surgical balloon for insertion into a uterus, comprising:

a substantially continuous outer wall defining an exterior surface of the balloon on a first side and an interior hollow of the balloon on a second side, the outer wall being formed from a stretchable elastic material and being stretchable by pressure within the inner interior hollow between a collapsed state and an expanded state;

the substantially continuous outer wall having a base portion for coupling with a catheter, and an end portion at a distal end of the balloon, and left and right extensions configured for insertion into the uterine cornua when the surgical balloon is in the expanded state, the extensions being spaced from each other and lying on either side of the end portion, wherein the end portion has a primary wall thickness less than a primary wall thickness of the base portion, and the left and right extensions have a primary wall thickness less than the primary wall thickness of the end portion.

9. The surgical balloon according to claim 8, wherein the end portion is at least substantially hemispherical in shape.

10. The surgical balloon according to claim 9, wherein the end portion is substantially symmetrical about a distal point of the balloon.

* * * * *